United States Patent
Freeman et al.

(10) Patent No.: US 12,203,549 B1
(45) Date of Patent: Jan. 21, 2025

(54) METHOD OF INTERFACING NONSPECIFIC CONDUITS BETWEEN THERMALLY INSULATED GASEOUS ENVIRONMENTS

(71) Applicants: George Leonard Freeman, Knaresborough (GB); Albert William Houghton, Sheffield (GB); Carl Heimann, Sheffield (GB); Jakub Jasik, Sheffield (GB); Adam Mitchell, Sheffield (GB); Poppy Culshaw, Sheffield (GB); Adam Glen, Sheffield (GB)

(72) Inventors: George Leonard Freeman, Knaresborough (GB); Albert William Houghton, Sheffield (GB); Carl Heimann, Sheffield (GB); Jakub Jasik, Sheffield (GB); Adam Mitchell, Sheffield (GB); Poppy Culshaw, Sheffield (GB); Adam Glen, Sheffield (GB)

(73) Assignee: Unicorn Biotechnologies Ltd., Sheffield (GB)

( * ) Notice: Subject to any disclaimer, the term of this patent is extended or adjusted under 35 U.S.C. 154(b) by 0 days.

(21) Appl. No.: 18/800,073

(22) Filed: Aug. 11, 2024

Related U.S. Application Data

(63) Continuation of application No. 18/431,960, filed on Feb. 3, 2024.

(51) Int. Cl.
*F16J 15/02* (2006.01)

(52) U.S. Cl.
CPC ........... *F16J 15/022* (2013.01); *F16J 15/028* (2013.01)

(58) Field of Classification Search
CPC ........... F16J 15/02; F16J 15/022; F16J 15/028
See application file for complete search history.

(56) References Cited

U.S. PATENT DOCUMENTS

2015/0374383 A1* 12/2015 Bödewadt ........ A61B 17/12145
606/157
2016/0081680 A1* 3/2016 Taylor ................ A61B 17/0057
606/213

\* cited by examiner

*Primary Examiner* — Gilbert Y Lee
(74) *Attorney, Agent, or Firm* — Eric P. Mirabel

(57) ABSTRACT

Disclosed is a system and method for sealing an opening through the boundary of a controlled thermal and gaseous environment such as an incubator or refrigerator, where conduit channels of arbitrary size and number are transferred across the boundary. A silicone or polymeric tube with flanges at either end is passed through the boundary opening, fixing one side to the boundary wall and attaching the other to a mechanism that controls or constrains the rotation of the tube. This is achieved by rotating or twisting one end of the tube, creating a hyperboloid-like structure that will seal around the conduits and thereby seal the opening. To further improve thermal efficiency, insulating material such as expanded polystyrene beads are placed into the space between the silicone or polymeric tube and the wall of the incubator, providing thermal stability that cannot be achieved by conventional conduit transferring methods.

24 Claims, 9 Drawing Sheets

Fig. 1A.
Fig. 1B.
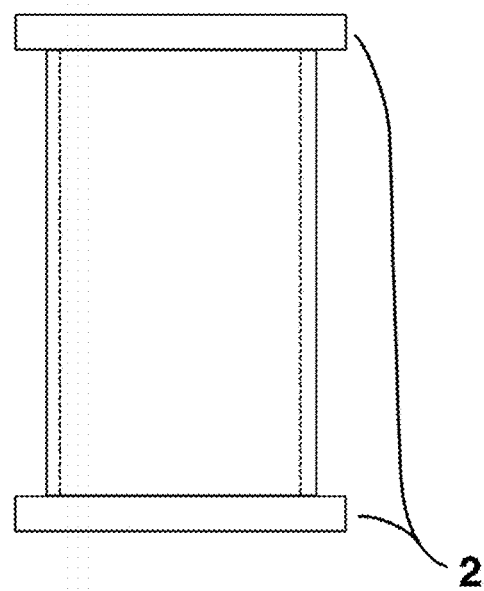
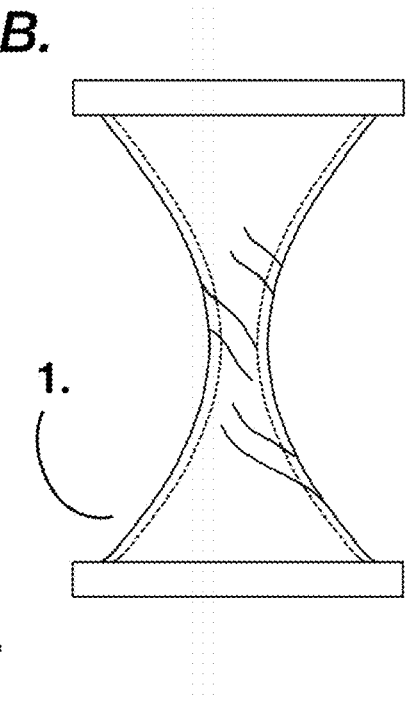
1.
2.
Fig. 1C.
Fig. 1D.
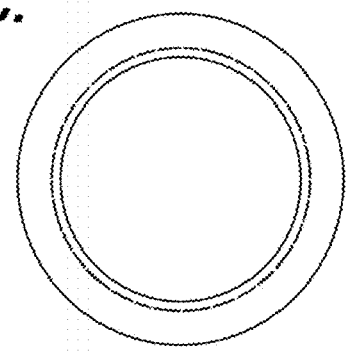
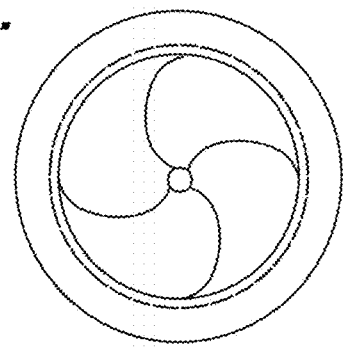

Fig. 2A.
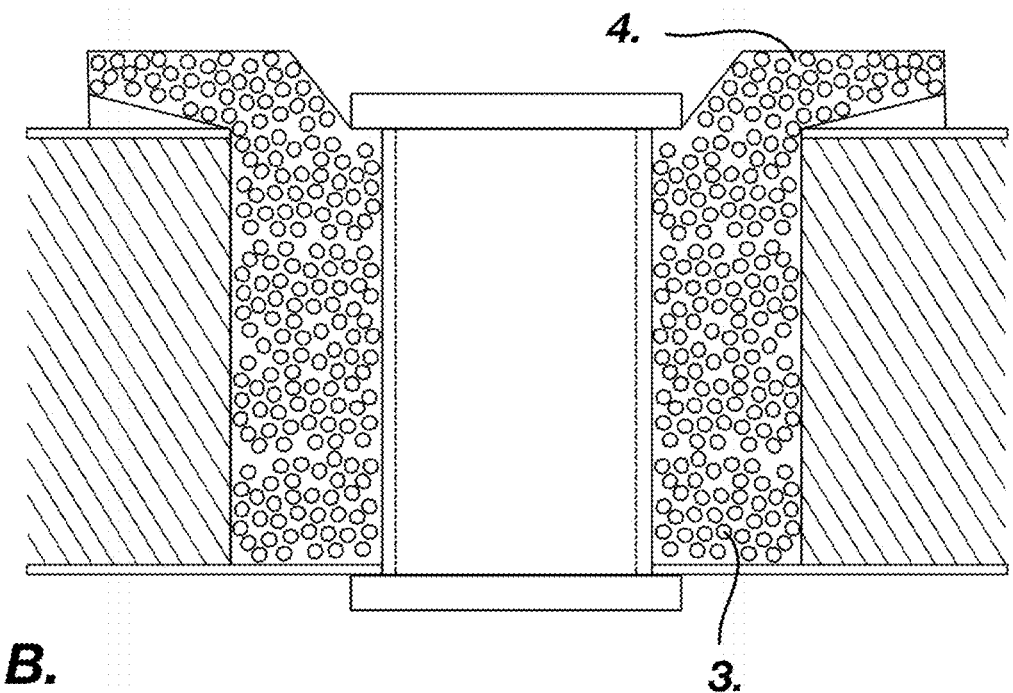
Fig. 2B.
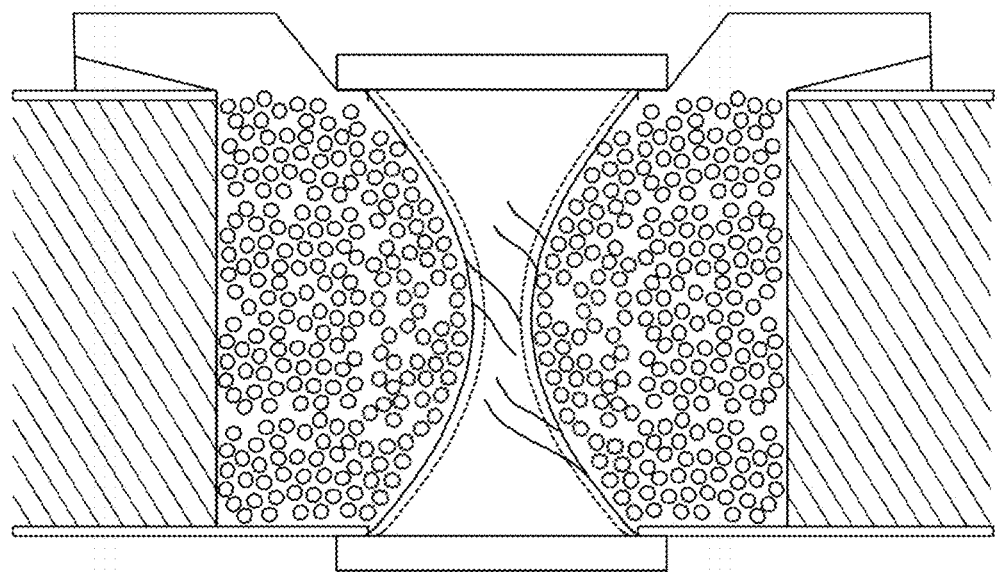

Fig. 7A.
Fig. 7B.
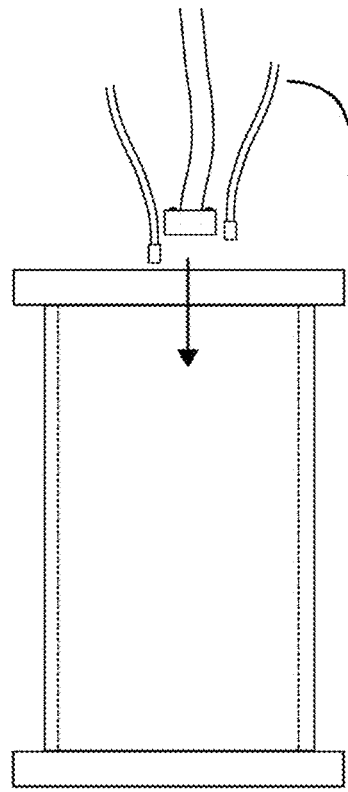
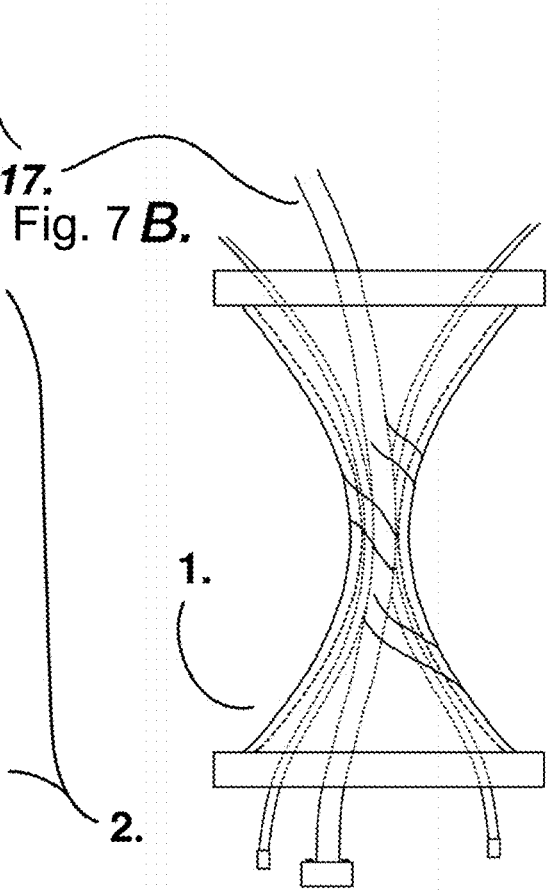
Fig. 7C.
Fig. 7D.
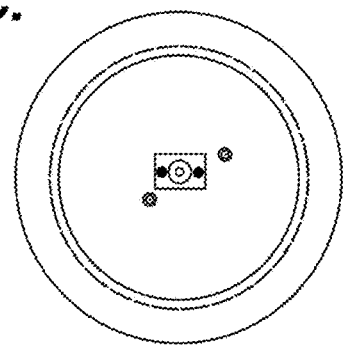
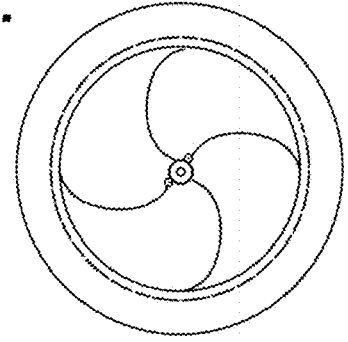

FIG 8

Open Hyperboloid

Rotate flanges of tube
Can be achieved by:
- Manual rotation of flanges/carrier
- Disconnection from holding mechanism, allowing elastic potential energy of tube to drive rotation
- Rotation driven by attached mechanism
- Autonomously driven upon command or external trigger Silicone tube untwists until fully open Insulating material pushed into overflow

↓

Material passed through opening

Material can be passed between environments through the opening. Such materials include:
- Conduits either autonomously or manually
- Instruments for manipulation such as robot arms or forceps
- liquids/gasses passively or by pressure difference

↓

Close Hyperboloid

Rotate flanges of tube
Can be achieved by:
- Manual rotation of flanges/carrier
- Rotation driven by attached mechanism
- Autonomously driven upon command or external trigger Silicone tube untwists until fully closed
Can seal around conduits if passing through or until closed if not Insulating material pulled into cavity
layer of insulating material occupies the former opening, aiding with thermal regulation Key
—— Hyperboloid operation
---- Sub steps and variable means of operation

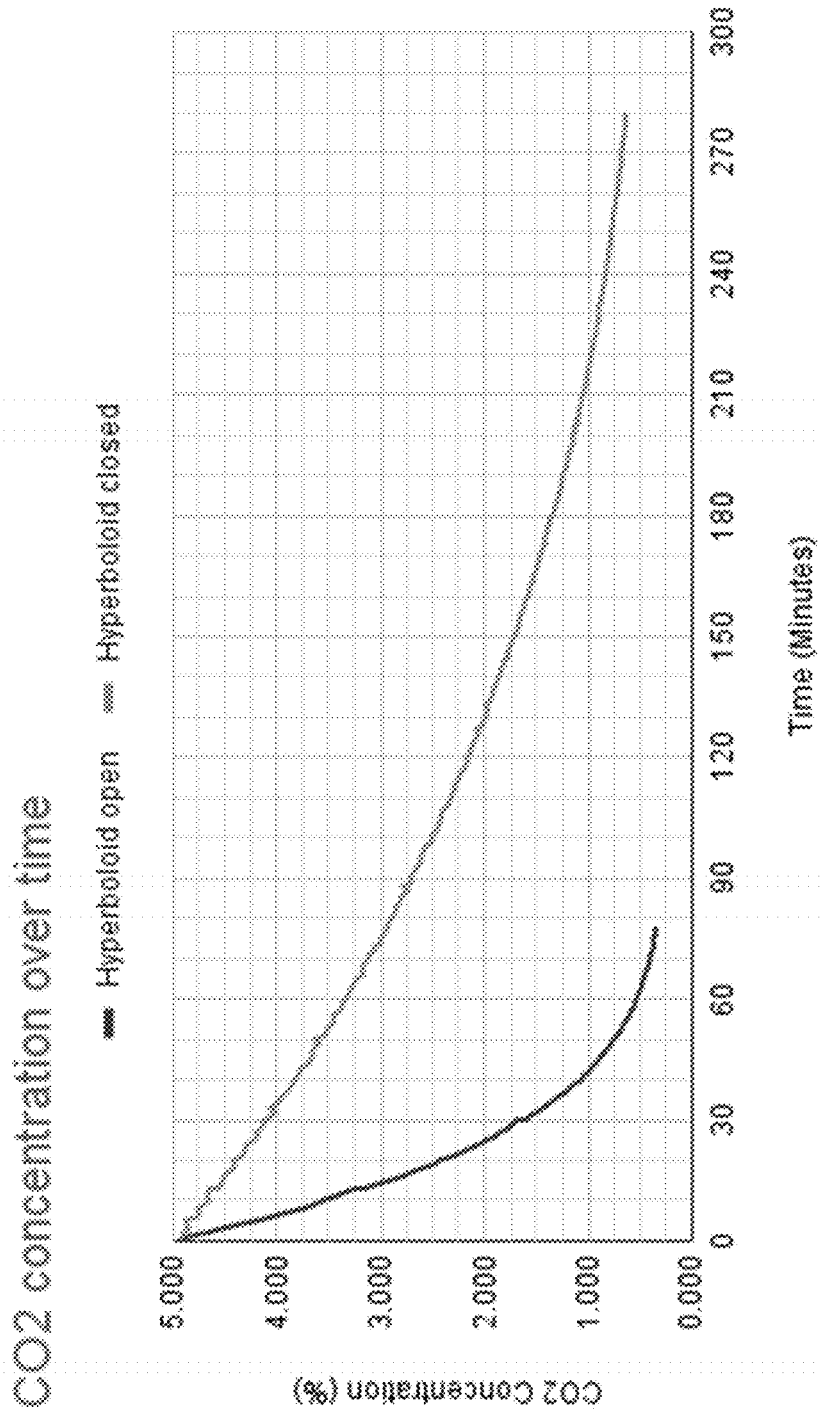

METHOD OF INTERFACING NONSPECIFIC CONDUITS BETWEEN THERMALLY INSULATED GASEOUS ENVIRONMENTS

BACKGROUND

As technological innovation in life science and biomanufacturing-related industries advances, the complexity of experimental protocols for mammalian cell and other cell culture based experiments and industrial production processes is increasing. Conventional paradigms of leaving well plates, flasks or other experimental or production-grade cell culture vessels unattended in a thermally insulated environment with controlled gaseous composition (e.g. an incubator or refrigerator) between stints of interaction in an uncontrolled environment (e.g. a lab bench) are not able to meet the increasingly stringent requirements for cell culture during research protocols and production processes.

Sensors for the real-time monitoring of supplied media and reagents, cell culture vessels, and in-line and off-line sampling of the cell culture and cell culture media are progressively being adopted by researchers and industry to inform experimental protocols, monitor outcomes for industrial applications, and drive optimized production processes. Furthermore, considerations that take a more proactive approach to cell culture in basic and applied research and industrial applications, such as mechanobiology, require additional equipment and infrastructure to perform cell culture operations beyond that which can be achieved with conventional thermally insulated environment with controlled gaseous composition cell culture instrumentation such as a cell culture incubator (see e.g., Heracell® $CO_2$ Incubators by ThermoFisher Scientific).

Consequently, the need to add additional devices and sensors inside gaseous-controlled instrumentation to interact with cell cultures and their associated reagents, vessels, and tools is becoming ever more important. However, in order to operate, these devices and sensors need to be physically placed inside the instrumentation, requiring said devices and sensors, as well as their wiring and or tubing (herein referred to as 'conduits') for the exchange of reagents, to be passed through the wall or exterior of the instrumentation.

The standard approach of adding additional devices and sensors to an instrument, most commonly an incubator, is to have a hole, generally in the rear, of the incubator that normally remains sealed with a silicone plug. This can either be left unsealed, used with a custom moulded plug, or with some means of sealing around generic conduits such as bristles or compliant foam. Except for custom moulded plugs, these solutions are ineffective at sealing the environment with both thermal losses and $CO_2$ leakage being a prevalent issue. Consequently, the diameter of these interfaces is typically small (>100 mm diameter) which limits the area through which gasses and heat can escape. However, it also serves to limit the number and size of the conduits that can be passed in and out of the incubator. This limitation inhibits progress in fundamental research, and in implementing more efficient and automated processes for commercial applications that can increase cell culture product quality and decrease production costs.

The development of a means to better seal around a larger range of a variety of conduits while minimizing thermal losses and gas leakage has the potential to advance fundamental cell culture based research and industrial cell culture based manufacturing by facilitating the use of a greater range of technologies within a thermally insulated environment with controlled gaseous composition, critical for use in cell culture environments, such as freezers, refrigerators and incubators.

A method to achieve this would be required to facilitate a larger aperture size to not only accommodate larger or more conduits, but also the connection mechanisms attached to them which are typically far larger than the conduits themselves. Furthermore, the method would be required to comply with and surround the cross section created as the conduits intersect the wall of the incubator such that the unwanted egress at the interface between the seal and the conduits are minimized. Finally, the means of sealing must consider thermal losses through conduction, particularly where the size of the aperture is large, the insulation typically provided by the thermally insulated wall will be lost. Consequently, the system must include the means of creating a barrier for the minimization of conductive heat loss while sealing around the conduit(s).

Hyperboloid-like structures have in recent years been identified as a practical means of creating a sealed environment from a larger aperture. This can be seen in their commercial use as a lid for a beverage container (Neolid, TWIZZ Cup, https://www.neolid.com). However, in this application, control of the thermal environment is limited to its use as a barrier for the egress of gas or liquid, with space constraints being a priority in the design. Furthermore, the use of a hyperbolid here has a use case limited to sealing around a single conduit (a drinking straw). Where thermal insulation is a more significant factor (as with refrigerators and incubators), a means to decrease the thermal conductivity across the sealed aperture is perhaps more important than reducing the volume of the sealing mechanism, particularly where the boundary walls are themselves thicker and decrease the thermal losses. These considerations allow for the use of a less space-constrained implementation of a hyperboloid based sealing mechanism, i.e., one that instead prioritises the minimisation of thermal losses.

SUMMARY

This invention is a convenient method of creating a thermal and gaseous seal around conduits for connections between walls or at the interior and exterior of, a thermally insulated environment housing a controlled gaseous composition, such as an incubator, freezer or refrigerator. The invention makes use of a silicone or polymeric tube with flanges at both ends. As the tube is twisted the polymeric tube stretches and forms a hyperboloid-like structure, sealing around any conduits passing through the center of the tube. A ratchet system (or similar mechanical device for constraining the direction of rotation until directed otherwise) is used to hold the hyperboloid-like structure in a twisted position sealed around the conduits. The elasticity of the polymeric tube can return the tube to its open position once the constraining mechanism is released.

Further to this, the system can provide further improved thermal insulation by at least filling the cavity surrounding the silicone or polymeric tube (preferably leaving a region for overfill in both its open and closed configurations) with a granular insulating material (such as expanded polystyrene beads) such that the material fills in the cavity as its volume increases when the hyperboloid is formed, thereby maintaining a layer of thermal insulation to minimize conductive heat loss across the aperture between the silicone or polymeric tube and the wall it passes through.

BRIEF DESCRIPTION OF DRAWINGS

FIG. 1A is an elevational view of the silicone or polymeric tube in its open configuration.

FIG. 1B is an elevational view of the silicone or polymeric tube when twisted, creasing the silicone or polymer and reducing the diameter of the tube towards the middle.

FIG. 1C is a plan view of the silicone or polymeric tube when open.

FIG. 1D is a plan view of the silicone or polymeric tube when twisted closed, creasing the silicone or polymer and reducing the diameter of the tube towards the middle.

FIG. 2A is an elevational view of the silicone or polymeric tube embedded in an insulated wall, shown in cross section, surrounded by granular insulated material. Excess granular insulated material is housed above the tubing within an 'overflow.'

FIG. 2B is the same view as in FIG. 1A but the silicone or polymeric tube is twisted to the hyperboloid formation.

FIG. 7A is an elevational view of an open silicone or polymeric tube showing conduits of various sizes and configurations positioned above the central bore.

FIG. 7B is the same elevational view as in FIG. 7A with the silicone or polymeric tube twisted closed, and with the conduits passed through the aperture, which preferably took place while the tube was open.

FIG. 7C is a plan view of an open silicone or polymeric tube showing conduits of various sizes and configurations passed through the aperture, as in FIG. 7B.

FIG. 7D is a plan view of the closed silicone or polymeric tube and the conduits, both as positioned in FIG. 7B.

FIG. 8 is a flow diagram detailing the stages, substeps and variables involved in the operation of the invention.

FIG. 9 is a graph comparing the $CO_2$ concentrations in a 0.1 m$^3$ container with the sealing system positioned on the roof of the container creating a hole of 8 cm diameter, when open. The internal $CO_2$ concentration was first brought up to 5% and then allowed to naturally drop, first with the sealing system open and then with the system closed. The open system drops five times more quickly from 5% to 2.5% demonstrating the sealing effectiveness of the system.

DETAILED DESCRIPTION

Figure 3A:
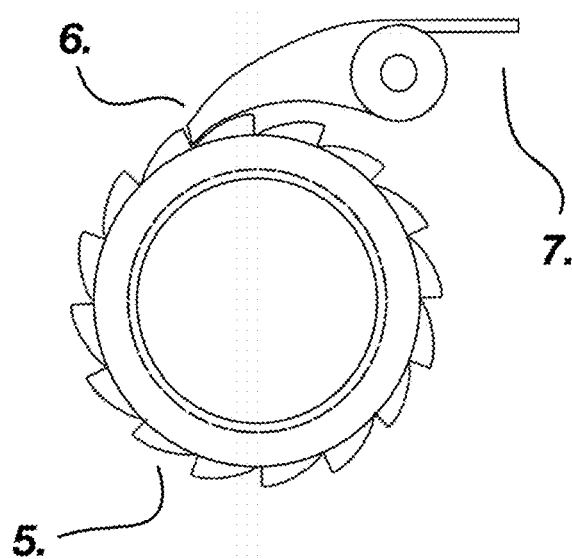
FIG. 3A is a plan view of an open silicone or polymeric tube, with an attached ratchet mechanism.

Referring to FIGS. 1A and 1C, the silicone or polymeric tube 1 is initially in its open state, through which conduits such as tubing for the transmission of liquid, gaseous or other matter states, electrical wiring and any other materials for transmitting data or information (e.g. fiberoptics), can be passed through. The silicone or polymeric tube can be made out of any elastic material (e.g. silicone) that can repeatedly be expanded and contracted without compromising the mechanical properties necessary to maintain a thermal and gaseous seal against items passed through the tube. Flanges 2 are attached to the silicone or polymeric tube and may be made of the same material, forming a continuous structure. The flanges serve to provide structural support and a means through which the tube can be manipulated. By rotating either or both of the flanges 2 as in FIGS. 1B and D, the silicone or polymeric tube 1 is twisted until it is sealed shut (closed). Regardless of the number or diameter of the conduits (provided when grouped, their cross-sectional size allows them to fit within the silicone or polymeric tube 1 opening), in its twisted configuration the silicone or polymeric tube 1 will seal around the conduits, leaving only the gaps in between individual conduits as a potential source of leakage.

FIG. 2 illustrates the addition of a granular insulating material 3 (such as expanded polystyrene beads) surrounding the exterior of the silicone or polymeric tube 1. FIG. 2A illustrates the presence of an overflow 4, for the housing of excess insulating material 3. As the silicone or polymeric tube 1 is twisted closed, the volume taken up by the silicone or polymeric tube 1 is reduced, and the material 3 will settle such that there is insulation surrounding the silicone or polymeric tube 1 and the conduits passed through it. In order to enhance insulation of the cavity, additional insulating material 3 can be supplied through an overflow 4, which thereby enables insulating material 3 to expand into the available volume as the silicone or polymeric tube 1 is twisted, and also provides a place for insulating material 3 to be pushed into when the tube 3 is restored to the open position.

Figure 3B:
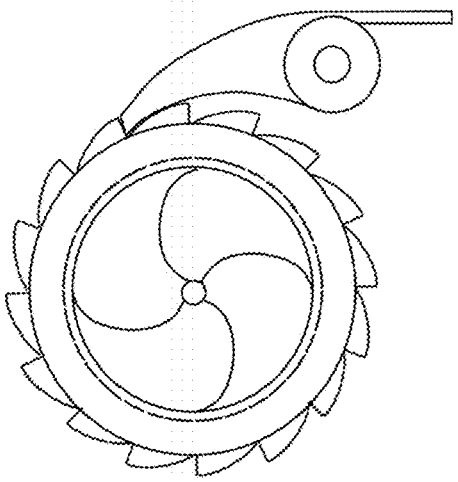
FIG. 3B is a plan view of the silicone or polymeric tube when closed, with an attached ratchet mechanism holding it in the closed position and preventing the elasticity of the silicone or polymer from returning the tube to its original position.

In order to create a seal, it is necessary to ensure that the twisted structure is constrained and does not loosen. This can be achieved through a ratchet mechanism as illustrated in FIG. 3. A ratchet 5 is connected to the flanges 2 in either a parallel or perpendicular configuration. When combined with a matching pawl 6, it can be used to constrain the direction of rotation of the silicone or polymeric tube 1 until the pawl is manually disconnected from the ratchet (using, e.g., a trigger 7), allowing the silicone or polymeric tube 1 to return to its open position. The pawl 6 is connected to a spring mechanism which ensures that it is continuously in contact with the ratchet mechanism. This mechanism allows the degree to which the silicone or polymeric tube 1 is twisted to vary depending on the volume or number of the conduits being passed through (where greater control can be exercised by increasing the number of teeth on the ratchet relative to the diameter), without negatively affecting the sealing.

Figure 4A:
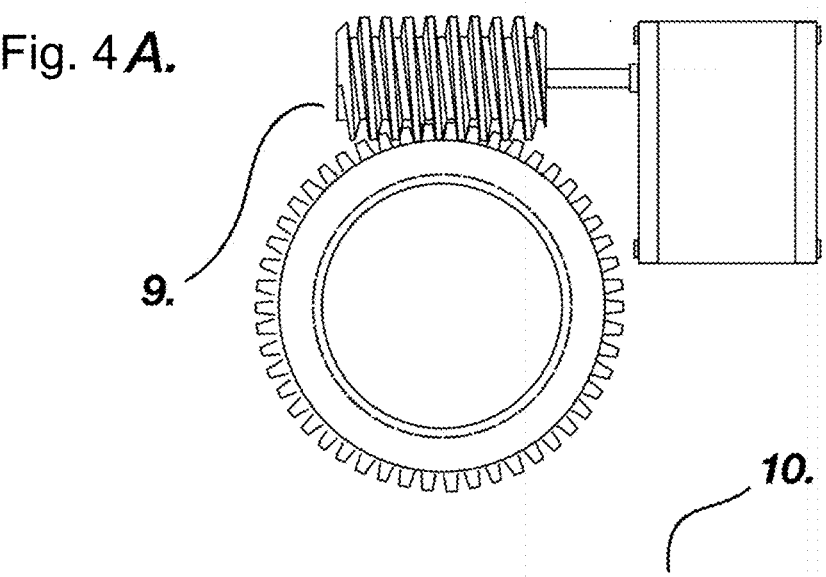
FIG. 4A is a plan view of an open silicone or polymeric tube, with an attached worm gear mechanism which is in turn connected to a driving mechanism which could be driven manually or by a motor.
Figure 4B:
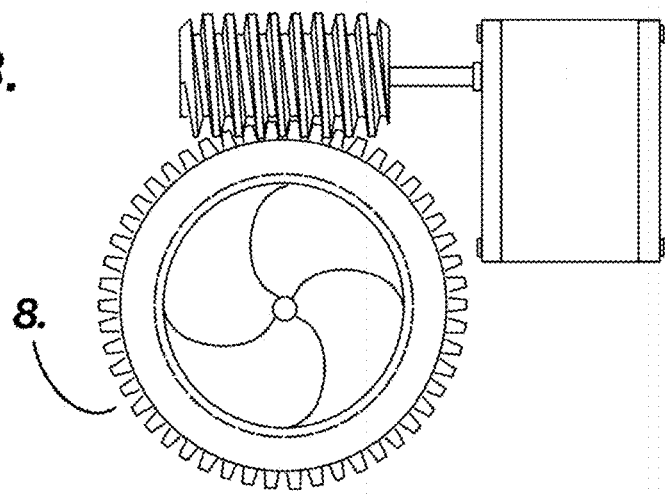
FIG. 4B is the same plan view as in FIG. 4A but with the silicone or polymeric tube twisted closed.

Other mechanisms can be used to constrain the rotation of the silicone or polymeric tube 1. FIG. 4 shows a worm gear 9 engaged with a gear 8 fixed to the flanges 2. The worm gear is able to prevent the tube's rotation in either direction. When the worm gear is driven, it moves and can twist or un-twisting the silicone or polymeric tube. The worm gear (or any other means of rotating the flanges 2) can be connected to a gearbox or other mechanism to provide actuation. Alternatively, it can be attached to a motor 10. In this way, the elasticity of the silicone or polymeric no longer controls the opening and closing of the tube (beyond supplying a force the control mechanism must be able to overcome) as motion is constrained in both directions of rotation.

Figure 5A:
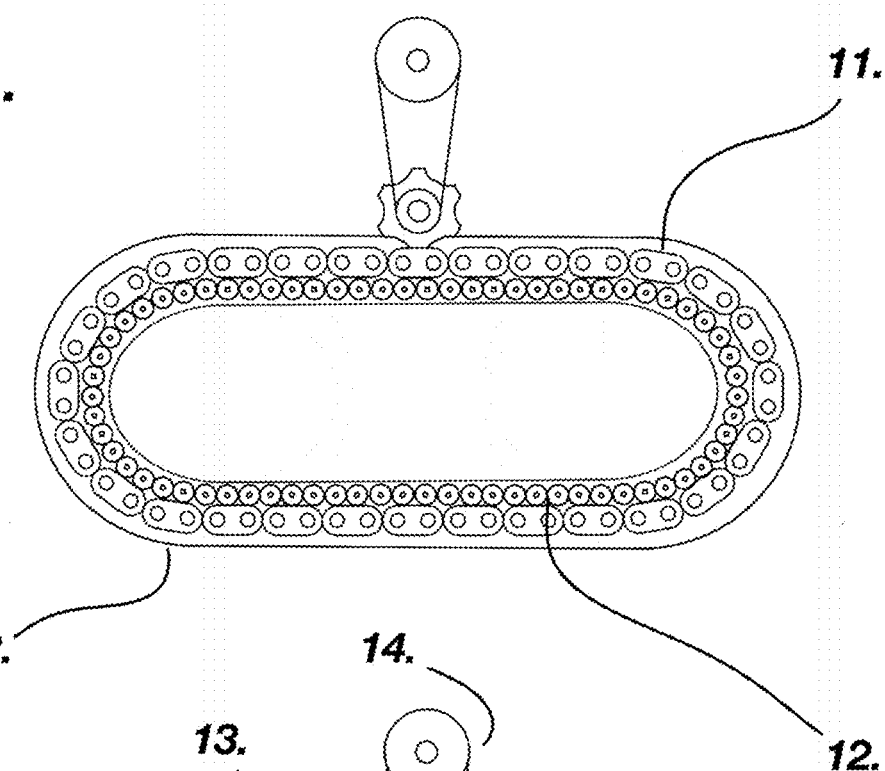
FIG. 5A is a plan view of an open silicone or polymeric tube, deformed into a 'stadium' shape through the use of a sequence of idlers, a chain attached to the silicone or polymeric tube, and a driving gear.
Figure 5B:
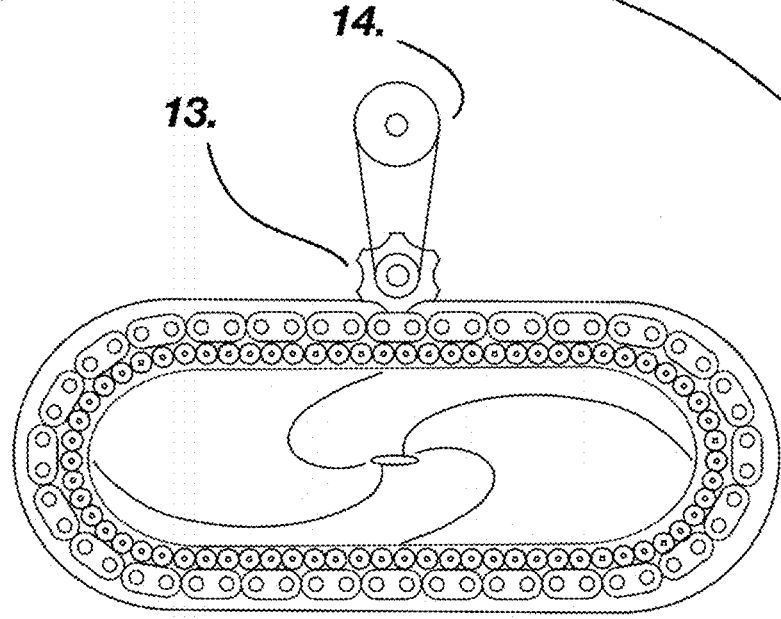
FIG. 5B is the same plan view as in FIG. 5A with the silicone or polymeric tube closed.

In some circumstances, a circular interface shape may not be appropriate, for instance, the wall geometry may be too narrow to accommodate a hole wide enough for specific conduits (or connecting ends). In these instances, it may be more appropriate to elongate the hyperboloid into another shape such as an oval or a stadium-like configuration. FIG. 5 shows how this can be achieved through the use of a sequence of idlers 12 arranged into the desired shape. Attached to the flanges and resting on the idlers is a chain 11 through which a gear 13 can drive the twisting of the silicone or polymeric tube by means of a connected mechanism 14, such as a motor. In this instance the silicone or polymeric tube can be formed such that it defaults to an oval or stadium shape in its natural configuration, or a silicone or polymeric tube of conventional cylindrical geometry can be deformed to produce this geometry.

Figure 6A:
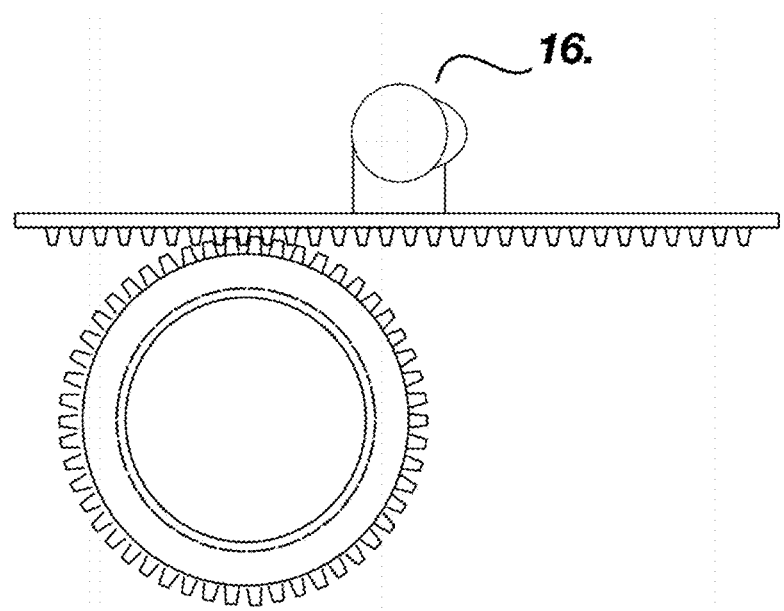
FIG. 6A is a plan view of an open silicone or polymeric tube, with an attached gear that is connected to a rack. The linear movement of the rack drives the rotational twisting of the tube to close it.
Figure 6B:
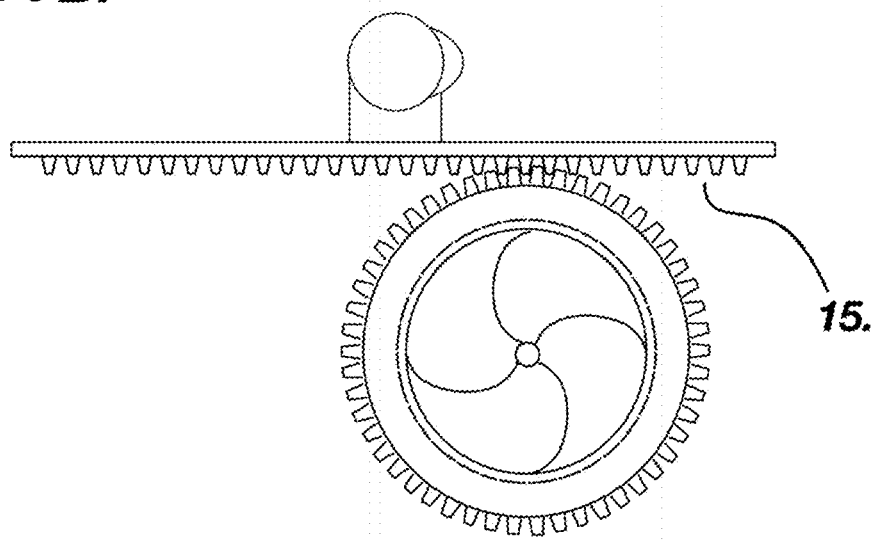
FIG. 6B is the same plan view as FIG. 6A, but with the rack driven to a position where the silicone or polymeric tube is closed.

The position, size, or application of a specific tube configuration may make the manual rotation of the silicone or polymeric tube non-viable, furthermore, autonomous rotation may also not be appropriate. In these instances, an alternative means of driving the twisting of the tube may be required. FIG. 6 shows one potential configuration to achieve this: i.e., the use of a rack 15 connected to a lever 16. When moved linearly, the rack 15 drives the rotation of the silicone or polymeric tube by means of an attached gear 8. Additional linkages (or a different mechanism) that may be more suitable, can be used to connect the lever to the rack or gear, depending primarily on the preferred degree of mechanical leverage.

The primary purpose of this invention is to allow for the interfacing of one or more conduits of various configurations and diameters to pass between the walls of a thermally insulated environment with a controlled gaseous composition, while maintaining a seal. FIGS. 7A to 7D illustrate conduits 17 extending through the silicone or polymeric tube followed by the sealing of the interface. In FIGS. 7B and 7D, the twisted silicone or polymeric tube 1 encapsulates the conduits and deforms around them to form a seal. For a desirable seal, the conduits should be capable of withstanding the external pressure supplied by the twisted silicone or polymeric tube, when a seal is formed. Alternatively, tube can be twisted to a lesser extent, thus reducing the air gap but not creating a seal.

The effectiveness of this method of sealing has been explored by reducing the rate of $CO_2$ loss both with the tube open and closed. FIG. 8 describes the process steps for the use of the invention to allow the passing of conduits into a thermally sealed environment with a controlled gaseous composition. FIG. 9 shows experimental data where the invention was integrated into an incubator system and the rate of $CO_2$ loss was measured. $CO_2$ loss was measured when the hyperboloid tube was open (representing common practices for transferring conduits into thermally sealed environments with a controlled gaseous composition) and when closed. The rate of $CO_2$ loss from an initial concentration within the incubator of 5% is significantly slower when the hyperboloid is closed, as opposed to when open. Specifically, the drop from 5% to 2.5% was five times slower when the sealing mechanism is engaged, as opposed to when there is no sealing mechanism around conduits.

Manipulation of the contents of a thermally sealed gaseous composition (e.g. the depositing and retrieval of samples, or simply, internal manipulation) is most typically achieved by opening the controlled environment to allow for operator access (e.g. opening the door on an incubator to enable a cell culture technician to manipulate cell culture vessels). However, this disturbs the controlled environment, which may in turn impact the experimental results or production process being utilised. Alternatively, robotic systems internal to the controlled environment that the silicon or polymeric tube is enabling conduit entrance into could be used (though only for manipulation) without the need to open the environment. However, this would quickly become cost prohibitive in the instance where there is a need of multiple separated environments which each require internal manipulation, as each would require a separate robotic systems. The invention could allow for the manipulation, deposition or retrieval from the environment while minimizing the disturbance, by providing an access port that can be configured around the manipulating object. The manipulating object could be, e.g., a human appendage of a technical operator, or a robotic arm or an automated fluidic control system. In the case where the invention is used for an incubator, this could allow for the addition and removal of sensors or tubing to tissue culture flasks, or the retrieval of samples or whole flasks.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of sealing an access to a thermally insulated container containing a controlled gaseous composition, comprising:
   providing a hyperboloid polymeric tube which extends through a wall of the thermally insulated container, having granular insulated material positioned between the exterior of the polymeric tube and the adjacent portion of the wall;
   providing at least one item extending through the bore of the tube; and
   twisting the tube in a first direction to cause it to constrict around the item and provide a seal around the item; and, optionally,
   twisting the tube in the opposite direction to open the tube.

2. The method of claim 1 wherein the polymer is silicone.

3. The method of claim 1 wherein the container is an incubator, refrigerator or freezer.

4. The method of claim 1 wherein the granular insulated material can flow in and out of a reservoir under the control of the relative degree of twisting of the tube.

5. The method of claim 4 wherein the granular insulated material flows out of the reservoir when the tube is closed, and into the reservoir when the tube is opened.

6. The method of claim 1 further including flanges at either end of the tube.

7. The method of claim 6 further including engaging the flanges or the tube to twist the tube.

8. The method of claim 1 wherein the items are conduits.

9. The method of claim 8 wherein the tube is opened to allow the addition, removal or repair of the conduits.

10. The method of claim 1 wherein the granular insulated material is expanded polystyrene beads.

11. The method of claim 1 for inputting or removing cell culture reagents including cell culture media and waste products.

12. The method of claim 1 for gaseous exchange.

13. The method of claim 1 wherein the gases exchanged include $CO_2$, $O_2$, atmosphere and any other gas or gaseous medium.

14. The method of claim 1 for the connection of two separate environments with heterogeneous controlled thermal and gaseous properties, including for venting an undesirable gaseous composition before resealing.

15. The method of claim 1 for providing a connection between sensors housed within a thermally sealed environment with a controlled gaseous composition.

16. The method of claim 15 wherein the sensors are for logging, tracking or controlling sensing data housed outside of the container.

17. The method of claim 1 further including fluidic conduits that interface directly with vessels for use in production methods.

18. The method of claim 1 wherein an operator without fully opening the environment manipulates a vessel, sensor or other device located inside the container.

19. The method of claim 1 wherein an automated system such as a robotic arm manipulates a vessel, sensor or other device located inside the container.

20. A method of sealing an access to a thermally insulated container containing a controlled gaseous composition, comprising:
  providing a hyperboloid polymeric tube which extends through a wall of the thermally insulated container, having granular insulated material positioned between the exterior of the polymeric tube and the adjacent portion of the wall;
  providing at least one item extending through the bore of the tube; and
  twisting the tube in a first direction to cause it to constrict around the item and provide a seal around the item; and, optionally,
  twisting the tube in the opposite direction, using gearing, chains, screws or a ratchet system, to open the tube.

21. The method of claim 20 further including a digital system that controls selective closing or opening and of the tube by controlling the system that twists and untwists the tube.

22. The method of claim 20 further including a lever or gearing system to assist in twisting the tube closed.

23. The method of claim 22 further including a motor, or pneumatic or hydraulic pressurizing device to drive the twisting of the tube.

24. The method of claim 20 further including an autonomous digital control system that can initiate opening or closing of the tube in the event of a trigger, which includes:
  the venting or exchanging of a gaseous environment in the event of unintended excessive heat generation or loss, or gas leakage leading to excess addition of gases;
  detection of the beginning or end of an experimental protocol, where opening and or closing is part of the automated disconnection and connection of one or more conduits; and
  to access containers, tissue culture flasks or vessels within a thermally insulated environment with a controlled gaseous composition without fully opening the system, or to pass controlled gaseous compositions through the tube between thermally insulated environments.

* * * * *